United States Patent [19]

Howard et al.

[11] Patent Number: 5,292,584

[45] Date of Patent: Mar. 8, 1994

[54] ULTRAHIGH MOLECULAR WEIGHT POLYETHYLENE AND LIGHTLY-FILLED COMPOSITES THEREOF

[75] Inventors: Edward G. Howard, Hockessin; Stuart M. Nemser, Wilmington, both of Del.

[73] Assignee: E. I. Du Pont de Nemours and Company, Wilmington, Del.

[21] Appl. No.: 683,930

[22] Filed: Apr. 11, 1991

[51] Int. Cl.$^5$ ............................................ B32B 5/16
[52] U.S. Cl. ............................. 428/327; 428/331; 428/332; 428/402; 428/407; 428/521; 526/352; 526/352.2
[58] Field of Search ............... 428/407, 327, 331, 332, 428/521, 402; 526/352, 352.2; 264/125, 126

[56] References Cited

U.S. PATENT DOCUMENTS

| | | | |
|---|---|---|---|
| Re. 31,992 | 9/1985 | Ancker et al. | 524/493 |
| 3,471,439 | 10/1969 | Bixler et al. | 524/586 |
| 3,519,593 | 7/1970 | Bolger | 524/461 |
| 3,847,888 | 12/1974 | Baumgaertner | 260/94.9 |
| 3,944,536 | 3/1976 | Lupton et al. | 528/503 |
| 3,975,481 | 8/1976 | Baumgaertner | 264/126 |
| 4,097,447 | 6/1978 | Howard | 260/421.4 |
| 4,104,243 | 6/1975 | Howard | 260/42.14 |
| 4,126,647 | 11/1978 | Howard | 260/878 R |
| 4,151,126 | 4/1979 | Adelman et al. | 252/508 |
| 4,187,210 | 2/1980 | Howard | 524/730 |
| 4,234,659 | 11/1980 | Kostandov et al. | 428/403 |
| 4,281,070 | 7/1981 | Scheetz et al. | 525/1 |
| 4,330,573 | 5/1982 | Kostandov | 427/213 |
| 4,769,433 | 9/1988 | Chanzy et al. | 526/348.1 |
| 4,933,393 | 6/1990 | Toyota et al. | 525/240 |
| 4,972,035 | 11/1990 | Suga et al. | 526/125 |
| 4,983,693 | 1/1991 | Haag et al. | 526/124 |
| 5,041,473 | 8/1991 | Gau et al. | 523/330 |

FOREIGN PATENT DOCUMENTS

| | | |
|---|---|---|
| 0376503 | 7/1990 | European Pat. Off. |
| 51-21910 | 2/1976 | Japan |
| 60-177047 | 9/1985 | Japan |
| WOA87/03288 | 6/1987 | PCT Int'l Appl. |

OTHER PUBLICATIONS

Han et al., *J. Macromol. Sci–Phys.*, B19(3):313 (1981).
Krishnamurthy et al., *Poly. Eng. Sci.* 29(8): 564 (1989).
Eur. Polym. J. vol. 24, No. 7, pp. 657–660, 1988.
Chemical Abstracts, vol. 92, No. 4 Jan. 1990, abstract No. 92:23173X.
Makromol. Chem., Rapid Commun. 3, 483–488 (1982).
Eur. Polym. J. vol. 26, No. 11, pp. 1161–1166, 1990.

*Primary Examiner*—Paul J. Thibodeau
*Assistant Examiner*—Hoa T. Le

[57] ABSTRACT

Homogeneous, particulate composites are provided, of about 75–99.5 weight percent ultrahigh molecular weight polyethylene (UHMWPE) and about 0.5–25 weight percent of at least one filler compound, and wherein the composites have a surface area of at least about 4 m$^2$/g. The particulate UHMWPE is also provided without the filler. Dense, load-bearing articles of these materials are formed by cold-pressing and free-sintering procedures. Cold-pressable, free-sinterable blends of commercial UHMWPE containing at least 25 weight percent of the composites or unfilled UHMWPE of the invention are also provided.

25 Claims, No Drawings

ULTRAHIGH MOLECULAR WEIGHT POLYETHYLENE AND LIGHTLY-FILLED COMPOSITES THEREOF

FIELD OF THE INVENTION

This invention relates to lightly-filled ultrahigh molecular weight polyethylene composites, unfilled ultrahigh molecular weight polyethylene, and their fabrication to dense shaped articles by cold-pressing and free-sintering.

BACKGROUND OF THE INVENTION

Ultrahigh molecular weight polyethylene (UHMWPE) composites are known. U.S. Pat. Nos. 4,097,447 (Howard), 4,126,647 (Howard), 4,151,126 (Adelman and Howard), 4,187,210 (Howard) and 4,104,243 (Howard) disclose homogeneous composites of polyolefins, including UHMWPE, with a variety of finely-divided particulate inorganic filler compounds, including alumina, calcium carbonate, kaolinite clay, mica and conductive carbon, and organic filler materials such as polyacrylonitrile, wherein the composites comprise at least about 25% by weight of filler. The aforementioned patents also disclose methods of preparing composites which permit relatively high loadings of filler without sacrifice of essential physical properties. In these processes ethylene is polymerized onto the surface of the filler particles such that the resultant composite is substantially free of polymer-free filler and of filler-free polymer. U.S. Pat. Nos. 4,330,573 and 4,234,659 disclose composites wherein a polyolefin having a molecular weight not less than 300,000 is polymerized onto a solid porous inorganic carrier material to provide composites wherein the inorganic carrier content is 50 to 99.5% by weight.

One important advantage of these mineral-/UHMWPE composites containing high levels of filler is that they can be fabricated into dense, homogeneous articles by the procedures of cold-pressing and free-sintering. By "cold-pressing" is meant forming an article under pressure at a temperature below the melting point of the polymer. By "free-sintering" is meant that no restraint is applied on the article during the hot-fusing (sintering) cycle.

Unfilled particulate UHMWPE in contrast cannot be fabricated into high density articles by this procedure unless its morphology and particle size meet stringent requirements. U.S. Pat. Nos. 3,847,888 and 3,975,481 disclose UHMWPE powders which are cold-pressable and free-sinterable at temperatures well above the crystalline melting point of the polymer, the powders having particles of less than 100 microns mean particle size and a size distribution function of less than 0.80. The required fine powders were prepared by extensive grinding of coarse virgin polymer, a procedure known to degrade molecular weight and related properties of UHMWPE. K. S. Han et al., J. Macromol. Sci.-Phys., B19(3), 313 (1981) disclose that polyethylene morphology is at least as important as particle size in determining sinterability and that only UHMWPE powders having a fibrous morphology provide good mechanical properties after sintering. Han et al., also disclose sinterable composites of UHMWPE with fibrous fillers, glass and graphite.

Japanese Kokai 51-21910 describes a porous sintered product suitable for printer rollers prepared by sintering mixtures containing 50–95% of UHMWPE having an average particle size of 3–6 microns and an apparent specific gravity of 0.30–0.40 g/cc, and 5–50% of UHMWPE having an average particle size of 100–300 microns and an apparent specific gravity of 0.15–0.20 g/cc. The sintered product is highly porous with pore sizes of 15 to over 40 microns. This reference also discloses that the more finely powdered UHMWPE component is easily sinterable alone while the coarser component is not sinterable. The component UHMWPEs were prepared by a low-pressure, Ziegler-catalyzed process, but UHMWPE synthesized by other techniques are said to be suitable for preparing sinterable mixtures.

U.S. Pat. No. 4,972,035 discloses UHMWPE fine powders having an average particle diameter of about 1–80 microns at least 20 weight percent of which passes through a 350 Tyler mesh screen. The products have bulk densities in the range of 0.1–0.5 g/ml and are said to provide molded articles having excellent physical properties. The UHMWPE powders are prepared by polymerizing ethylene in a dispersion of a special Ziegler catalyst comprising a titanium compound supported on magnesium chloride particles plus an organoaluminum co-catalyst. The requisite powder is formed by either shearing the UHMWPE product or by shearing the supported Ziegler catalyst to fine powder prior to polymerization. While the present invention employs a Ziegler type catalyst, the polymerization is homogeneous such that all catalyst components are dissolved in the polymerization solvent.

U.S. Pat. No. 4,983,693 discloses a process for preparing UHMWPE by polymerizing ethylene with a supported Ziegler catalyst comprising titanium tetrachloride supported on a special alumina and an aluminum alkyl, e.g. triethylaluminum. A hydrocarbon solvent such as n-hexane is used. The special alumina support has a surface area of 200–400 $m^2/g$, pore volume of 1.5–3.5 ml/g and 85% of the pores exceed 100 Å in size. The molar ratio of Al/Ti in the catalyst is in the range of 2.5/1 to 80/1. The UHMWPE products have a bulk density of at leas 0.3 g/ml and 85% of the particles are 13–32 microns in size. No information on processability of the products is provided.

V. Krishnamurthy et al., Poly. Eng. Sci., 29 (8), 564 (1989) disclose that problems of long process time and non-uniform heating in the sintering of UHMWPE powders can be overcome to some extent by employing a conductive iron filler and sintering by induction heating. Filler level was 10 volume percent, sufficient to completely coat all polymer particles with iron. Unexamined Japanese Kokai Patent Number 60-177047 discloses sinterable compositions comprising 100 parts by weight of UHMWPE, 5–100 parts by weight of an inorganic fiber of selected length and aspect ratio, and 0.005–0.2 parts by weight of an organic peroxide.

The references discussed herein suggest that highly-filled UHMWPE composites are readily processed without any significant loss of physical properties. While some references teach a limited processability of lightly filled or unfilled UHMWPE, it is apparent that such efforts have not been highly successful. Therefore there exists a strongly felt need for unfilled UHMWPE and lightly-filled UHMWPE composites that are as readily processable into articles by cold-pressing and free-sintering as is highly-filled UHMWPE, said articles exhibiting properties which equal or exceed those of articles prepared by extrusion or molding at high temperatures.

It is an object of the present invention to provide composites of UHMWPE and low percentages of filler compound that unexpectedly meet the aforementioned requirements. It is a further object of the present invention to provide non-fibrous, particulate, unfilled UHMWPE having a large surface area and that also unexpectedly meet the aforementioned requirements. A feature of the present invention is the provision for articles manufactured with the composites and UHMWPE herein using the well-accepted techniques of cold-pressing and free-sintering. An advantage of the present invention is the provision for dense, sintered articles exhibiting properties common to melt-processed UHMWPE. These and other objects, features and advantages will become readily apparent upon having reference to the description of the invention herein.

SUMMARY OF THE INVENTION

This invention provides a homogeneous, particulate composite comprising (a) about 75–99.5% by weight of ultrahigh molecular weight polyethylene having a molecular weight of at least 800,000, and (b) about 0.5–25% by weight of at least one finely-divided, filler compound having a neutral-to-acidic surface, in which substantially all of said polyethylene is polymerized onto the surface of said filler, and substantially all of said filler has polyethylene polymerized thereon, said composite having a surface area of at least about 4 $m^2/g$.

The present invention also provides a non-fibrous, particulate ultrahigh molecular weight polyethylene having a molecular weight of at least 800,000, a surface area of at least about 4 $m^2/g$ and a bulk density of less than 0.2 g/ml.

The present invention further provides compositions consisting essentially of commercial UHMWPE containing at least 25% by weight of the non-fibrous, particulate ultrahigh molecular weight polyethylene of the invention, or of the homogeneous, particulate composite of the invention, said compositions being processable by cold-pressing and free-sintering to dense, load bearing articles.

The present invention still further provides dense articles (including prosthetic articles, seals and the like) fabricated by cold-pressing and free-sintering these composites, polyethylenes and mixtures.

DETAILED DESCRIPTION OF THE INVENTION

The composites of this invention comprising UHMWPE and one or more inorganic filler compounds may be prepared by the methods described for more highly-filled polyolefin composites in the aforementioned U.S. Pat. Nos. 4,097,447; 4,126,647; 4,151,126; 4,187,210; and 4,104,243, all of which are hereby incorporated by reference herein. In the processes of these patents, the polyolefin is polymerized directly onto finely-divided filler particles the surfaces of which have been chemically treated with a catalytically active amount of a transition metal compound. A particularly useful method of preparing suitable finely-divided filler is described in U.S. Pat. No. 4,104,243.

Preferably the present composites contain less than 20 weight percent filler, more preferably less than 7 weight percent filler. Particularly preferred embodiments of this invention are UHMWPE particulate composites containing less than 3 weight percent filler compound, or unfilled particulate UHMWPE having a surface area of at least 4 $m^2/g$, said embodiments being fabricable into dense articles by cold-pressing and free-sintering. By "dense" is meant a specific density of at least 0.9 g/ml. The composites containing 0.5–2 weight percent filler, prepared in accordance with the aforementioned procedure, have essentially the bulk properties of unfilled UHMWPE. The unfilled particulate UHMWPE and lightly-filled composite of this invention are non-fibrous. Commercial UHMWPE and the UHMWPE constituent of the present composites have molecular weights in excess of 800,000, preferably at least 4,000,000, and have a melt index (ASTM D1238) of essentially zero and very high inherent viscosity. Such polymers are highly viscous in the molten state, making melt processing difficult.

Preferably, in the composites of the present invention, the finely divided filler compound has a weight-average equivalent spherical particle diameter of 0.1 to less than 50 microns, and the catalytically active amount of transition metal compound interacted at the filler surface provides 0.000001–1.7 mg-atom of transition metal per gram of filler, and said composite is a free-flowing powder having particle sizes in the range of 0.1 micron to 5 mm and an average particle size of in the range of about 2 to 50 microns. The free-flowing powdered composites of the invention typically have a 10-second micronization homogeneity of at least 50% and a micronization homogeneity index of at least 20. Preferably the transition metal is selected from the group consisting of titanium, zirconium and chromium.

Two or more starting composites having different properties may be blended together as described in U.S. Pat. No. 4,187,210 (column 18, lines 34–50) to provide a new composite having properties intermediate to those of the constituent composites. Numerous additives can also be blended with the UHMWPE/filler composites as described in U.S. Pat. No. 4,187,210 (column 18, line 51 to column 19, line 20), for purposes of stabilization against UV radiation, oxidation, biodegradation and the like.

Inorganic filler compounds useful in preparing the present composites include those described in U.S. Pat. Nos. 4,187,210 (column 8, line 49 to column 9, line 48); 4,097,447 (column 3, lines 32-48); and 4,151,126 (column 4, line 54 to column 5, line 43). Certain organic fillers such as polymers may also be used as described for polyacrylonitrile in aforesaid U.S. Pat. No. 4,126,647, providing ethylene can be polymerized onto the surfaces of said fillers. Suitable fillers will normally have the characteristics described in U.S. Pat. No. 4,187,210 (column 10, line 31 to column 14, line 49). Representative fillers for the present invention include alumna hydrates, silicas, water-insoluble silicates, calcium carbonate, basic aluminum sodium carbonates, hydroxyapatite and calcium phosphates. Preparation of composites containing at least 25 weight percent filler is described in U.S. Pat. No. 4,187,210 (column 14, line 50 to column 17, line 60).

The unfilled particulate UHMWPE of the invention is prepared by coordination polymerization of ethylene in solution in the presence of an unsupported transition metal compound such as titanium tetrachloride and a suitable organoaluminum compound such as trialkylaluminum, especially triethylaluminum. The polymerization is carried out in an inert hydrocarbon solvent in which the catalyst system and unpolymerized ethylene are soluble. The transition metal compound may be employed in the amount of about 0.01 to 1 mg-atom of transition metal per mole of polymerized ethylene. The aluminum alkyl may be employed in the amount of about 1 to 50 mmoles per mg-atom of transition metal, preferably about 5 to 20 mmoles per mg-atom of transition metal. The polymerizations are carried out in at least a 2-fold excess, by weight, of solvent with respect to the total amount of ethylene added.

Preferably, in the preparation of UHMWPE of the invention containing no filler, the polyethylene has a molecular weight of at least about 1,000,000, the transition metal is titanium and the aluminum alkyl is triethylaluminum. The preferred average particle size for unfilled UHMWPE is at least 100 microns. The unfilled UHMWPE of the invention has a bulk density of less than about 0.2 g/ml, preferably about 0.1 g/ml or less. Preferred unfilled UHMWPE of the invention has a surface area of at least 5 $m^2/g$.

It has also been discovered that mixtures containing as little as 25% by weight of the unfilled UHMWPE of this invention, or the lightly-filled composites of this invention, can be processed by cold-pressing and free-sintering to high density, load-bearing articles having mechanical properties similar to those of commercial UHMWPE processed by the more costly melt extrusion methods. Preferred mixtures contain about 40–60% by weight of the UHMWPE of the invention.

The compositions of the invention, being fabricable by relatively inexpensive cold-pressing and sintering methods, are useful in all applications requiring the excellent mechanical and load-bearing properties and chemical inertness of UHMWPE including hydraulic cylinders, gears, sprockets, pulleys, sheaves, wheels, rollers, machinery carriages, conveyor equipment components, bearings, seals, washers, bushings, gear racks, skis, guides, textile machine parts, and in biomedical applications such as prosthetic articles and orthopedic joint and bone replacement parts. In bone replacement applications, suitable mineral filler compounds include hydroxy apatite, a calcium phosphate, and phosphated calcium carbonate, compounds which are fully compatible with natural bone.

Methods of shaping (forming) composites of the invention are described in the aforementioned patents, for example, U.S. Pat. No. 4,187,210 (column 19, line 21 to column 21, line 5).

The compositions of this invention are also suitable starting materials for making unusually tough, creep-resistant (enhanced) UHMWPE compositions and articles by processes involving programmed application of heat and pressure described in pending patent applications U.S. Ser. No. 500,053 filed Mar. 23, 1990, U.S. Ser. No. 500,054 filed Mar. 23, 1990 and U.S. Ser. No. 564,144 filed Aug. 7, 1990, the disclosure of which is hereby incorporated by reference.

EXAMPLES

In the following examples of the invention Examples 1–4 describe the preparation of a cold-pressable and free-sinterable UHMWPE composite with filler; Example 5 a cold-pressable and free-sinterable UHMWPE without filler; and Comparative Examples 1–3 commercial compositions. All parts and percentages in this section are by weight unless otherwise specified. Unless otherwise noted, triisobutylaluminum is added as a 1.6M solution in n-heptane. Filler content of the composites was determined as described in U.S. Pat. No. 4,187,210. Polyethylene molecular weight was estimated from its hot flow characteristics. UHMWPE shows little or no tendency to flow when melted. In the examples physical properties are determined by the following ASTM test designations:

| Property | Test Specification |
|---|---|
| Tensile Strength, max. (T) | ASTM D638-71A |
| Tensile Modulus, initial | ASTM D638-71A |
| Flexural Modulus | ASTM D790-71 |
| Elongation at Break | ASTM D638-71A |
| Izod Impact Strength | ASTM D256-72A |

In the tensile, elongation and modulus tests, test bars of Type I and Type V of ASTM test method 638-72 and bars prepared according to ASTM test method 638-44T were used.

In the examples, density of compressed, shaped product was determined by measuring the weight and volume of the shaped product, or by means of a density gradient column. Bulk density of virgin product was determined by weighing 100 ml of said product. Surface areas of composites and unfilled products of the invention were determined by the B.E.T. method on virgin polymer. Somewhat lower surface areas values may be obtained from samples which have been heated, for example to outgas or dry prior to surface area measurements. However, the fabricability of these compositions into high quality, dense, load-bearing articles by cold-pressing and free-sintering is not impaired by such heating provided the heating temperature is well below the melting point of the polyethylene.

EXAMPLE 1

A polymerization mixture was prepared by dispersing 20 g of Englehard ASP ® 400 clay, previously dried for 17 hours at 150° C. under nitrogen, in 500 ml of dry, oxygen-free cyclohexane containing 5 mmoles of triisobutyl-aluminum and 0.2 mmol of tetraneophylzirconium. The mixture was treated with an ethylene pressure of 1.38 MPa at 60° C. for 12.5 hours. The product weighed 125 g and contained 16 weight percent clay.

The product was cold-pressed at 3.45 MPa and at 138 MPa into 1¼ in diameter cylinders. The cylinders were placed in a jar and sintered under nitrogen for 1 hour in an oven at 160° C., then allowed to cool slowly. The densities of all cylinders were determined by weighing and measuring cylinder volumes. Density results are given in Table 1.

COMPARATIVE EXAMPLE 1

Hoechst Hostalen ® GUR-412 commercial grade UHMWPE was cold-pressed and sintered according to the conditions of Example 1. Density results are given in Table 1, and surface area results in Table 2.

COMPARATIVE EXAMPLE 2

Himont 1900 commercial grade UHMWPE was cold-pressed and sintered according to the conditions of Example 1. Density results are given in Table 1, and surface area results in Table 2.

COMPARATIVE EXAMPLE 3

Allied AC 1220 commercial grade UHMWPE was cold-pressed at 166 MPa and sintered according to the conditions of Example 1. The sample has a fibrous morphology. Density results are given in Table 1.

EXAMPLE 2

Example 1 was repeated except that 20 g of Englehard Satintone ® No. 1 calcined clay was used. The polymerization consumed 80 g of ethylene in 3 hours, 7 min. The product weighed 103 g and contained 19 weight percent clay. Density results are given in Table 1.

EXAMPLE 3

Example 2 was repeated except that 10 g of Englehard Satintone ® No. 1 calcined clay and 4 mmoles of triisobutylaluminum were used. The polymerization consumed 86 g of ethylene in 21.5 hours. The product weighed 103.2 g (9.7 weight percent clay). A (separate) sample was hot-pressed to a strong, smooth, difficult-to-tear film. Density results are given in Table 1.

EXAMPLE 4

A polymerization mixture in a 1-gallon autoclave was prepared by dispersing 4 g of fumed alumina (Degussa), previously dried for 1 hour at 150° C. under nitrogen, in 3 liters of dry, oxygen-free cyclohexane containing 0.17 g (0.9 mmoles) of titanium tetrachloride and 7 mmoles of triisobutylaluminum. Polymerization was carried out at 50°–57° C. under an ethylene pressure of 690 kPa for 1 hour, 26 min, during which time 200 g of ethylene was consumed. The filtered and dried product weighed 205 g, contained 2 weight percent alumina, and was powdery with a bulk density of 0.108 g/ml.

A sample of the product was heated to a temperature above the melting point of the constituent polyethylene and pressed into a film. The molten polymer flowed very little, indicating very high molecular weight. The film was strong and most of the alumina was uniformly dispersed.

A one-inch diameter cylinder about 0.5 in. high was prepared by cold-pressing the powdered product under 34.5 MPa pressure for 15 min, followed by free-sintering at 160° C. for 2 hours under nitrogen. The cylinder, containing no voids visible to the naked eye, had an average density of 0.9050 g/ml as determined by density gradient column.

EXAMPLE 5

This Example describes the preparation of a cold press/sinterable ultrahigh molecular weight polyethylene containing no filler.

A dry, oxygen-free 1-gallon autoclave was charged with a solution of 0.2 ml (1.8 mmole) titanium tetrachloride in 3 l of dry, oxygen-free cyclohexane and 10 mmoles of triethylaluminum was added. The reactor was closed rapidly, stirring was started and ethylene was added at 50 psi (345 kPa) pressure. Polymerization was allowed to continue for 85 minutes and produced 177 g of fine, white powdered polymer. The polymer particles produced were soft and easily pressed together. When hot pressed, the molten polymer showed very low flow, indicating ultrahigh molecular weight. Bulk density of the product was 0.07 g/ml. About 75% of the powdered product passed through 20 mesh U.S.S. but was retained on 140 mesh U.S.S. (104 microns).

A 3 in x 3 in×0.125 in (7.6 cm×7.6 cm×0.32 cm) plaque was hot pressed for 2 min under 3000 psi (21 MPa) pressure (Sample 5-H). A second plaque of similar dimensions was cold pressed under 20,000 psi (138 MPa) pressure for 2 min, removed from the mold and sintered between stainless steel plates at 160° C. for 30 min. The plates and plaque were then wrapped in insulation and allowed to cool slowly (Sample 5-CPS). Both samples had a density of 0.93 g/ml. Density data are compared with other UHMWPE's in Table 1.

Tensile and impact properties determined on tensile bars (TYPE V) and Izod impact bars cut from each plaque showed little difference between the samples (Table 2).

For comparison, Hoechst Hostalen ® GUR-415 commercial UHMWPE powder was cold pressed under 20,000 psi (138 MPa) pressure to give a weak green form. This was heated between stainless steel plates in an oven at 60° C. for 2 h. The plates and polymer were wrapped in insulation and allowed to cool slowly. The resultant plaque had a density of about 0.6 g/ml. Tensile and Izod impact bars were cut from the plaque (Sample G-CPS). A second batch of Hostalen ® GUR-415 was conventionally processed by commercial ram extrusion (Sample G-H). Tensile and impact results are given in Table 2.

Surface area of the total powdered product, determined by the B.E.T. method, is shown in Table 3 together with surface area data of commercial UHMWPE. None of the materials of Table 3 has a fibrous morphology; the Allied product cited in Table 1 has a fibrous morphology, according to the aforementioned Han et al. reference.

TABLE 1

| UHMWPE | SAMPLE DENSITY (g/ml) | | | $\frac{Dc - Do}{Dc} \times 100$ |
|---|---|---|---|---|
| | Calcd. | Cold Press 3.45 MPa | Pressure 138 MPa | |
| Hoechst Hostalen ® | | | | |
| GUR-412 | 0.94 | 0.67 | 0.68 | 27.7 |
| GUR-415 | 0.94 | — | 0.60 | 36.2 |
| Himont 1900 | 0.94 | 0.65 | 0.78 | 17.7 |
| Allied | | | | |
| AC 1220[d] | 0.94 | — | 0.90[a] | 4.3 |
| Example 1 | 1.04 | 1.03 | 1.05 | −1.0 |
| Example 2 | 1.07 | 0.45 | 0.99 | 7.4 |
| Example 3 | 1.00 | 1.01 | 1.03 | −3.0 |
| Example 4 | 0.96 | — | 0.91[b] | 5.2 |
| Example 5 | 0.94 | — | 0.93[c] | 1.1 |

Dc = Calculated Sample Density; Do = Observed Sample Density.
[a]Cold pressed at 166 MPa.
[b]Cold pressed at 34.5 MPa.
[c]Cold pressed at 103.5 MPa.
[d]No longer available commercially.

Calculated sample density was deduced from a knowledge of filler density, filler content and (unfilled) polyethylene density, prior to pressing and sintering.

TABLE 2

| Properties | 5-H | 5-CPS | G-H | G-CPS |
|---|---|---|---|---|
| Tensile (ASTM D638-71A) | | | | |
| Strength, yield, psi | 2762 | 2772 | 3418 | 504 |
| Strength, max, psi | 4669 | 4792 | 5113 | 508 |
| Strength, break, psi | 4689 | 4793 | 5113 | 508 |
| Elongation, yield, % | 15.8 | 13.9 | — | 11.7 |
| Elongation, break, % | 360 | 400 | 315 | 29.3 |
| Modulus, kpsi | 128.2 | 122.8 | — | — |
| Izod Impact (ASTM D256-72A) | | | | |
| Ft lb/in of notch | 16.7[a] | 17.6[a] | 18.4[a] | 0.44 |

[a]Non-break

TABLE 3

| UHMWPE or Composite | Surface Area m²/g |
|---|---|
| Hoechst Hostalen ® GUR 415 | 2.4 |
| Himont 1900 | <1 |

TABLE 3-continued

| UHMWPE or Composite | Surface Area m²/g |
|---|---|
| Example 5 | 5.7 |
| Example 6-1 | 5.8 |
| Example 6-2 | 4.7 |
| 75% Al₂O₃.3H₂O | 6.3 |
| 50% CaCO₃ | 9.0 |

EXAMPLE 6

Five samples of unfilled UHMWPE were prepared by an ethylene polymerization process similar to that used in Example 5 involving homogeneous catalysis with TiCl₄ and triethylaluminum in oxygen-free cyclohexane at 40°–50° C. Specific ethylene pressures and amounts of catalyst components are shown below:

| Sample | Ethylene, psi | TiCl₄, ml | AlEt₃, mmole |
|---|---|---|---|
| 6-1 | 150 | 0.2 | 10 |
| 6-2 | 200 | 0.2 | 10 |
| 6-3 | 50 | 0.35 | 10 |
| 6-4 | 50 | 0.3 | 10 |
| 6-5 | 50 | 0.15 | 10 |

Inherent viscosities (zero shear) and bulk densities of the products are shown in Table 4. Bulk densities of commercial UHMWPE are shown for comparison.

TABLE 4

| Sample | Inh. Viscosity | Bulk Density (g/ml) |
|---|---|---|
| 6-1 | 23.0 | 0.066 |
| 6-2 | 29.5 | 0.10 |
| 6-3 | 19.6 | — |
| 6-4 | 19.6 | 0.063 |
| 6-5 | 21.4 | — |
| Ex 5 | — | 0.070 |
| Hoechst Hostalen ® | | |
| GUR-412 | — | 0.472 |
| GUR-415 | — | 0.468 |
| Himont 1900 | — | 0.365 |

EXAMPLE 7

This Example shows that mixtures of unsinterable commercial UHMWPE containing at least 25% by weight of the unfilled UHMWPE of Example 6 (Sample 6-4) are cold press-sinterable.

The virgin powdered product 6-4 of Example 6 was mixed in a food blendor with commercial Hoechst Hostalen ® GUR 415 UHMWPE then (cold) pressed at room temperature under 99.4 MPa pressure into plaques having the dimensions 3 in×3 in×⅛ in (7.6 cm×7.6 cm×0.32 cm). Plaques of 3 blends were sintered at 175° C. and cut into Type V tensile bars and Izod impact bars and tested. Results are shown in Table 5.

TABLE 5

| Blend | 6-4 Content, wt % | GUR 415 Content. wt % |
|---|---|---|
| 7-1 | 50 | 50 |
| 7-2 | 25 | 75 |
| 7-3 | 10 | 90 |
| 7-4 | 0 | 100 |

| Properties | 7-1 | 7-2 | 7-3 | 7-4 |
|---|---|---|---|---|
| Tensile (ASTM D638-71A) | | | | |
| Strength, yield, psi | 2811 | 1980 | 591 | 504 |
| Strength, max, psi | 3855 | 2085 | 591 | 508 |
| Strength, break, psi | 3854 | 1940 | 279 | 508 |
| Elongation, yield, % | 10.0 | 43 | 6.7 | 11.7 |
| Elongation, break, % | 267 | 51.6 | 23 | 29.3 |
| Modulus, kpsi | 141.5 | 100.4 | 42.8 | — |
| Izod Impact (ASTM D256-72A) | | | | |
| Ft lb/in of motch | 17.4 | 2.9 | 0.40 | 0.44 |

It can be appreciated that the above-described examples are intended to be illustrative of, and not limiting, the invention described herein. Further, it is readily understood by those skilled in the art, there can be a variety and modifications to the invention as described and claimed herein without departing from the spirit and the scope thereof.

We claim:

1. A homogeneous, particulate, cold-pressable and free-sinterable composite comprising (a) about 75-99.5% by weight of ultrahigh molecular weight polyethylene having a molecular weight of at least 800,000 and (b) about 0.5-25% by weight of at least one finely-divided, filler compound having a neutral-to-acidic surface, in which substantially all of said polyethylene is polymerized onto the surface of said filler, and substantially all of said filler has polyethylene polymerized thereon, said composite having a surface area of at least about 4 m²/g.

2. The composite of claim 1 wherein the ultrahigh molecular weight polyethylene has a molecular weight of at least 4,000,000.

3. The composite of claim 1 wherein the ultrahigh molecular weight polyethylene has a melt index of essentially zero.

4. The composite of claim 1 wherein said filler is present in an amount of about 0.5-20% by weight.

5. The composite of claim 4 wherein said filler is present in an amount of about 0.5-7% by weight.

6. The composite of claim 5 wherein said filler is present in an amount of about 0.5-3% by weight.

7. The composite of claim 1 wherein said filler has a weight-average equivalent spherical particle diameter of 0.1 to less than 50 microns.

8. The composite of claim 1 wherein the particulate composite is a free-flowing powder having particle sizes in the range of 0.1 micron to 5 mm and an average particle size of about 2 to about 50 microns.

9. The composite of claim 8 wherein the free-flowing powder has a 10-second micronization homogeneity of at least 50% and a micronization homogeneity index of at least 20.

10. The composite of claim 1 wherein the filler compound is an inorganic compound selected from the group consisting of alumina hydrates, silicas, water-insoluble silicates, calcium carbonate, basic aluminum sodium carbonates, hydroxyapatite and calcium phosphates.

11. A load-bearing article having a density of at least 0.9 g/ml fabricated by cold-pressing and free-sintering the composite of claim 1.

12. The load-bearing article of claim 11 in the form of a seal.

13. A prosthetic article having a density of at least 0.9 g/ml fabricated by cold-pressing and free-sintering the composite of claim 1.

14. A cold-pressable and free-sinterable composition consisting essentially of non-sinterable ultrahigh molecular weight polyethylene and at least 25% by weight of the composite of claim 1.

15. A load-bearing article having a density of at least 0.9 g ml fabricated by cold-pressing and free-sintering the composition of claim 14.

16. A non-fibrous, particulate, cold-pressable and free-sinterable ultrahigh molecular weight polyethylene having a molecular weight of at least 800,000 and a surface area of at least about 4 m$^2$/g, a bulk density of less than 0.2 g/ml, and an average particle size of at least 100 microns.

17. The polyethylene of claim 16 having a molecular weight of at least 4,000,000.

18. The polyethylene of claim 16 having a bulk density less than or equal to 0.1 g/ml.

19. A load-bearing article having a density of at least 0.9 g/ml fabricated by cold-pressing and free-sintering the polyethylene of claim 16.

20. The article of claim 19 in the form of a prosthetic device.

21. The load-bearing article of claim 19 in the form of a seal.

22. The polyethylene of claim 16 having a melt index of essentially zero.

23. A cold-pressable and free-sinterable composition consisting essentially of non-sinterable ultrahigh molecular weight polyethylene and at least 25% by weight of the polyethylene of claim 16.

24. A load-bearing article having a density of at least 0.9 g/ml fabricated by cold-pressing and free-sintering the composition of claim 23.

25. A cold-pressable and free-sinterable composition consisting essentially of non-sinterable ultrahigh molecular weight polyethylene and at least 40% by weight of the polyethylene of claim 16.

* * * * *